United States Patent [19]

Brinkerhoff et al.

[11] Patent Number: 5,404,870
[45] Date of Patent: Apr. 11, 1995

[54] METHOD OF USING A TRANSANAL INSERTER

[75] Inventors: Ronald J. Brinkerhoff, New Richmond; Todd J. Olson, Loveland, both of Ohio

[73] Assignee: Ethicon, Inc., Cincinnati, Ohio

[21] Appl. No.: 257,464

[22] Filed: Jun. 9, 1994

Related U.S. Application Data

[63] Continuation of Ser. No. 68,226, May 28, 1993, abandoned.

[51] Int. Cl.[6] .......................................... A61M 29/00
[52] U.S. Cl. ........................................ 128/3; 606/191; 227/175; 227/179; 604/264
[58] Field of Search .................. 604/15, 106–109, 604/279, 170, 272, 264; 128/3; 606/197, 191, 198; 607/138; 227/175, 179

[56] References Cited

U.S. PATENT DOCUMENTS

| | | | |
|---|---|---|---|
| 668,879 | 2/1901 | Miller | 606/198 X |
| 3,895,634 | 7/1975 | Berger et al. | |
| 4,043,346 | 8/1977 | Mobley et al. | 606/198 X |
| 4,585,437 | 4/1986 | Simms | 604/106 |
| 4,650,459 | 3/1987 | Sheldon | 604/15 |
| 4,712,536 | 12/1987 | Hawks | 128/3 |
| 4,900,315 | 2/1990 | Lundqvist et al. | 604/15 |
| 4,957,486 | 9/1990 | Davis | 606/197 X |
| 4,973,302 | 11/1990 | Armour et al. | 604/15 |
| 5,104,025 | 4/1992 | Main et al. | 227/175 |
| 5,135,526 | 8/1992 | Zinnanti et al. | 128/3 X |
| 5,263,937 | 11/1993 | Shipp | 604/272 X |

FOREIGN PATENT DOCUMENTS

| | | | |
|---|---|---|---|
| 664359 | 9/1929 | France | 607/138 |
| 2708071 | 8/1978 | Germany | 128/3 |
| 391204 | 4/1933 | United Kingdom | 128/3 |

*Primary Examiner*—Michael H. Thaler
*Attorney, Agent, or Firm*—Dressler, Goldsmith, Shore & Milnamow, Ltd.

[57] ABSTRACT

A transanal inserter is disclosed which facilitates the atraumatic insertion of intra-anal surgical devices through the anus. The inserter has a tubular portion, a prolate distal end and a proximal end having a flange associated therewith. The prolate end is formed from a plurality of petal-shaped segments which deflect outward as an intra-anal surgical device is urged therethrough, into the colon or intestine. The flange formed at the proximal end of the inserter retains the inserter in place and prevents over insertion of the inserter beyond the anus. The inserter can be fabricated in varying lengths to accommodate surgical requirements. The inserter is fabricated from a plastic material with sufficient pliability to provide for deflection of the segments, while maintaining sufficient rigidity to prevent collapse of the inserter during insertion and use.

2 Claims, 2 Drawing Sheets

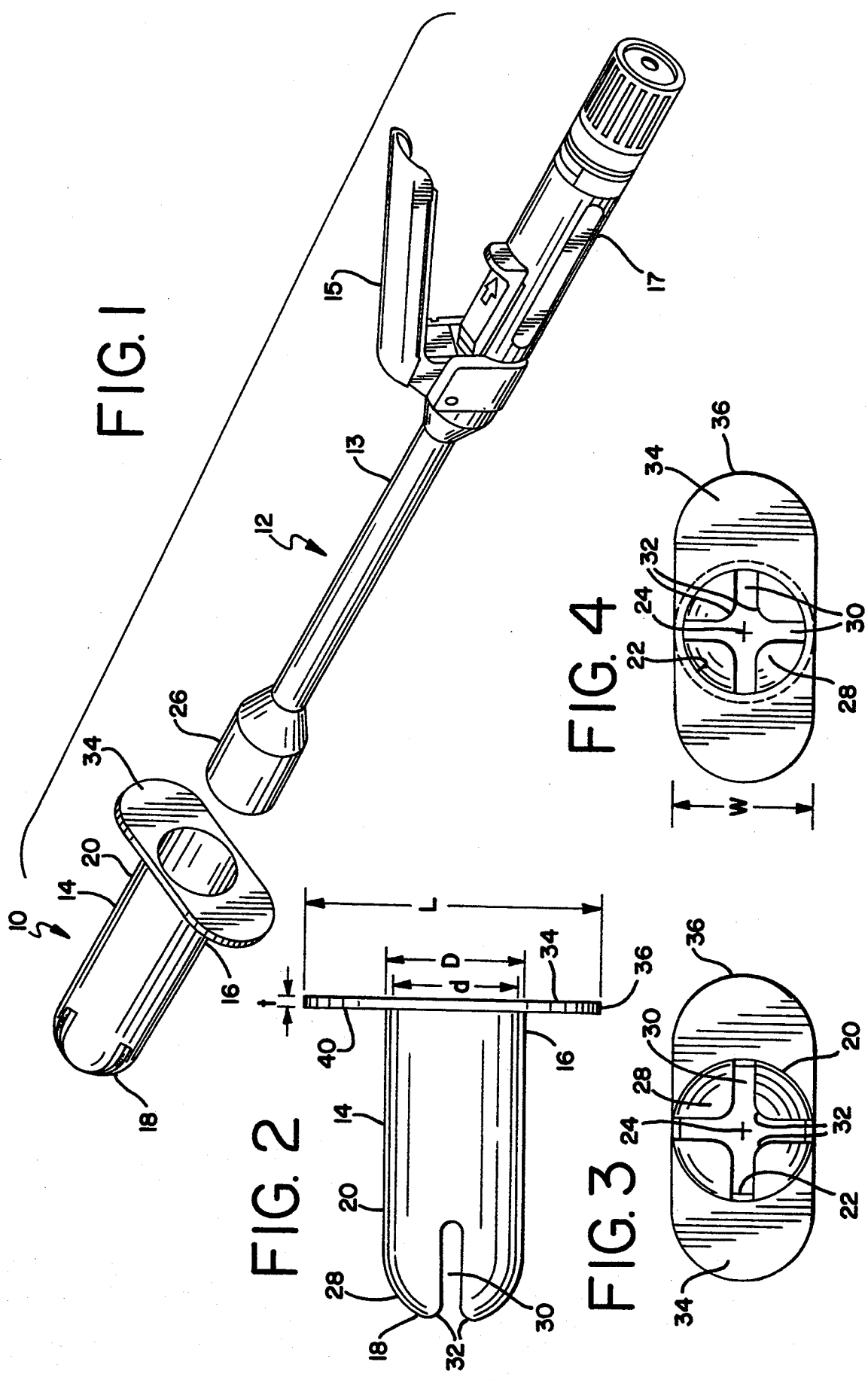

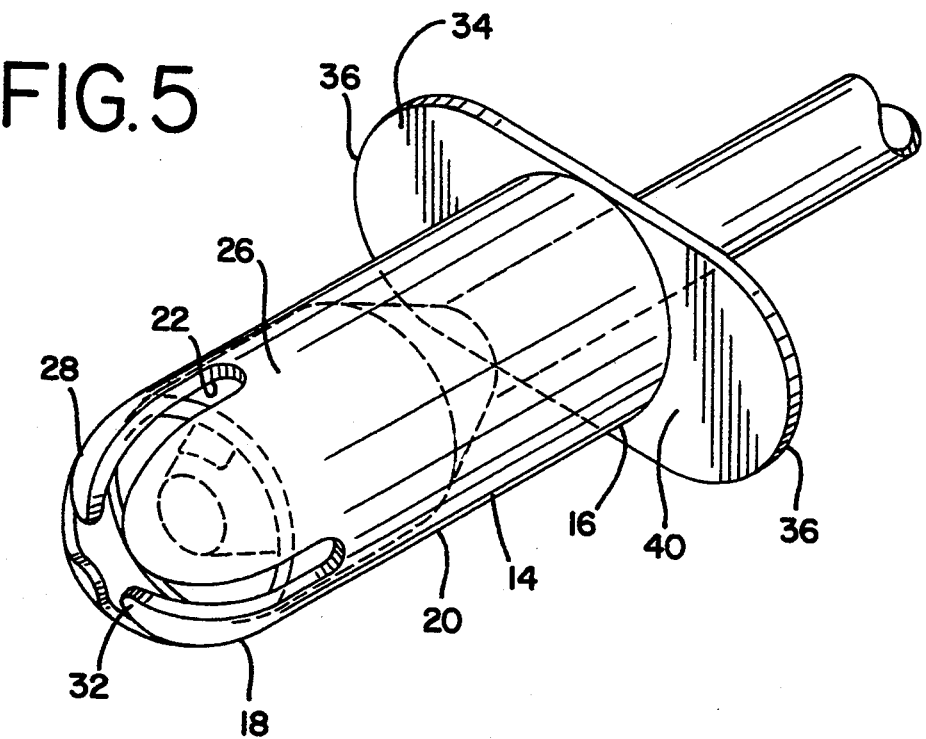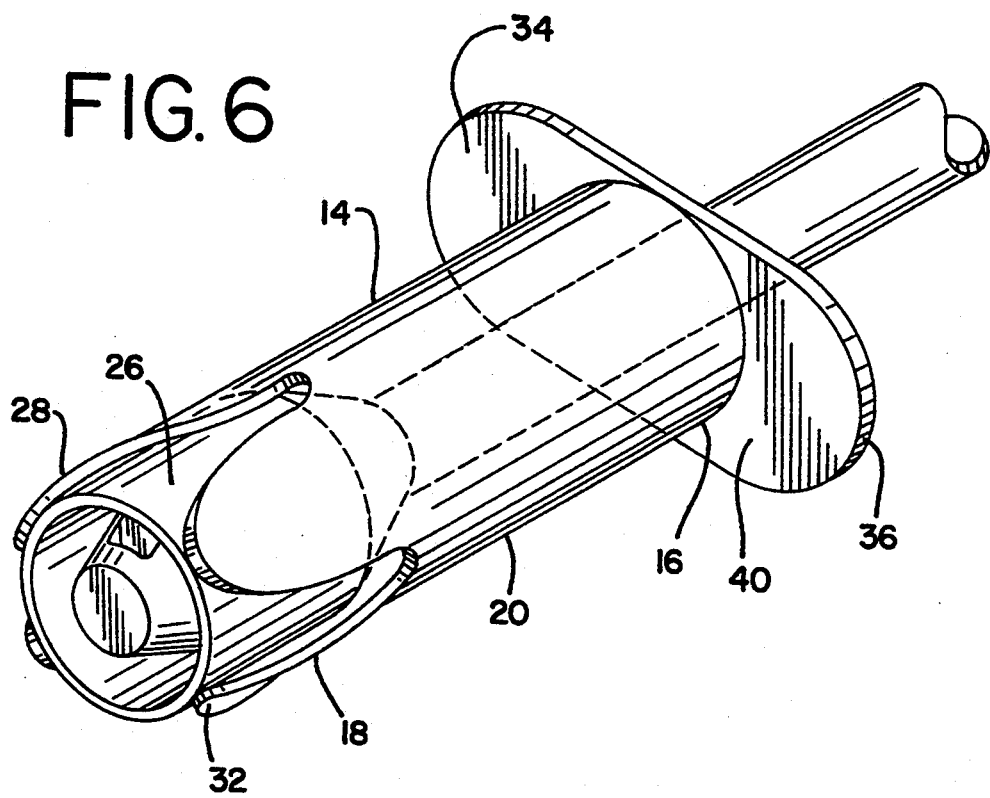

METHOD OF USING A TRANSANAL INSERTER

This application is a continuation of application Ser. No. 08/068,226, filed May 28, 1993, now abandoned.

FIELD OF THE INVENTION

This invention generally relates to surgical instruments; and more particularly, the invention relates to an inserter device for facilitating the atraumatic insertion of intra-anal surgical devices through the anus, into the colon or intestine.

BACKGROUND OF THE INVENTION

Presently, various intra-anal surgical devices, such as intraluminal anastomotic surgical staplers (hereinafter "ILS"), require insertion into the colon or intestine through the anus. Certain devices, such as the ILS, have anvil portions removably mounted to the distal end of the device. Generally, the ILS is inserted with the anvil portion attached, however, there are surgical procedures which require inserting the ILS without the anvil portion attached. Typically, the anvil portion is tapered inward toward the tip; however, the distal end portion may have a squared, non-tapered end.

Inserting the ILS into the colon or intestine, through the anus, with the anvil portion removed, may cause irritation and traumatic displacement of the surrounding tissue.

Devices are known in the art to assist in inserting squared end or non-lubricated objects into cavities within the body. Such devices include tampon applicators. However, such devices are not presently used for inserting surgical devices through the anus, nor do they provide a means to prevent over insertion into the body.

SUMMARY OF THE INVENTION

The transanal inserter device in accordance with the invention, engages the distal end of an ILS, or similar intra-anal surgical device, to ease insertion of the device through the anus and into the colon or intestine. The inserter is comprised of an integrally molded plastic inserter tube, having petal-shaped segments forming a prolate distal end, and a flange or stop at the proximal end.

The transanal inserter alleviates the tissue abuse known to accompany insertion of an anvil-less intra-anal device, by providing a soft, resilient, gradually tapered, prolate covering over the distal end of the device. The inserter guides the surgical device through the anus and into the tissue beyond, such that the surgical device does not contact the surrounding unaffected tissue. In addition, the transanal inserter has a flange or other means to retain the inserter in place and prevent over insertion thereof into the anus.

BRIEF DESCRIPTION OF THE DRAWINGS

A more complete appreciation of this invention, and many of the attendant advantages thereof, will be readily apparent as the same becomes better understood by reference to the following detailed description, when considered in conjunction with the accompanying drawings, in which like reference numerals indicate the same or similar components, wherein:

FIG. 1 is a perspective view of a transanal inserter device of the present invention shown near the distal end of an exemplary intraluminal anastomotic surgical stapler;

FIG. 2 is a side view of the transanal inserter device shown in FIG. 1;

FIG. 3 is a front view of the transanal inserter device shown in FIG. 1;

FIG. 4 is a rear view of the transanal inserter device shown in FIG. 1;

FIG. 5 is a perspective view of the transanal inserter, with the distal end of an ILS shown in broken lines, partially inserted into the inserter; and FIG. 6 is a perspective view of the transanal inserter, with the distal end of an ILS partially extending beyond the inserter and the petal-like segments deflecting outward.

DETAILED DESCRIPTION OF THE PREFERRED EMBODIMENTS

Referring generally to FIG. 1, there is shown a preferred embodiment of a transanal inserter device 10 in combination with an exemplary intra-anal surgical device, such as an intraluminal anastomotic surgical stapler ("ILS") 12. ILS 12 has a shaft 13, a trigger 15, a handle 17, and a distal end portion 26. Distal end portion 26 is intended to be inserted through the anus into the colon or intestine to a predetermined depth as necessary for particular surgical procedures. An example of an ILS device is disclosed in U.S. Pat. No. 5,104,025, to Main et al., for an Intraluminal Anastomotic Surgical Stapler With Detached Anvil, which patent is assigned to the same assignee as the present patent, the disclosure of which is incorporated herein by reference.

Referring to FIGS. 2–4, the transanal inserter device 10 has three principal sections: a hollow tubular section 14, a proximal end portion 16 and a distal end portion 18. The inserter 10 is preferably fabricated from a suitable moldable plastic material with sufficient pliability to provide for controlled deflection and sufficient stiffness to retain shape during insertion and use. Inserter 10 is preferably fabricated from polypropylene or like acceptable medical grade material capable of sterilization.

The hollow tubular section 14 has an outer surface 20 and an inner surface 22. Tubular section 14 may vary in length from about two (2) inches to about eight (8) inches as necessary for particular surgical procedures. The bore 24, defined by the diameter d across inner surface 22, is generally about three-fourths (¾) to about one and one-half (1½) inches depending upon the diameter of the distalend 26 of the cooperating ILS 12 or other devices.

Distal end portion 18 has a prolate shape, formed from a plurality of petal-shaped segments 28. When closed, the segments 28, form a prolate shape. Preferably, about three (3) to eight (8) segments 28 form distal end portion 18. Each of the segments 28 is separated by an open slot 30. The tip 32 of each of the segments 28 has rounded ends and rounded edges to eliminate sharp edges or pointed surfaces.

In a preferred embodiment, a flange 34 is formed integrally at the proximal end portion 16 of the inserter 10. Flange 34 has a distal surface 40. The width of flange 34 is substantially and conveniently the same as the outer diameter D of tubular section 14. Flange 34 is about three (3.0) inches in length (L) and about one-tenth (1/10) of an inch in thickness (t). The ends 36 of flange 34 are round or semi-circular to eliminate sharp edges or surfaces.

In use, an intra-anal device 12 is inserted into bore 24 of transanal inserter 10 such that the distal end 26 is positioned against the inner surface 22 at distal end portion 18, as seen in FIG. 5. Inserter 10 and intra-anal device 12 are then inserted through the anus until the distal surface 40 of flange 34 rests against the perineal tissue surrounding the anus, and distal end portion 18 extends to a predetermined depth within the colon or intestine as required by the surgical procedure. Alternatively, inserter 10 can first be inserted through the anus. Once the inserter 10 is in place, the distal end 26 of the ILS 12 can be inserted through the inserter 10 and into the colon or intestine.

In use in either manner, distal surface 40, which rests against the perineal tissue surrounding the anus, retains the inserter in place and prevents over-insertion of inserter 10 beyond the anus. As best seen in FIG. 6, as distal end 26 is urged forward against segments 28, the segments 28 deflect outward and allow distal end 26 to advance beyond the inserter 10 to the desired location.

Inserter 10 can be fabricated in different lengths as required by the surgical procedure, to position the distal end 26 of ILS 12 at the desired location within the colon or intestine. The thickness t and length L of flange 34 provide sufficient structural rigidity to prevent collapse of inserter 10 during insertion and subsequent forward movement of intra-anal surgical device 12.

From the foregoing it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modifications as fall within the scope of the claims.

What is claimed is:

1. A method for inserting the distal end portion of an intra-anal surgical stapling device through an anus comprising the steps of:
   a. positioning the distal end portion of an intra-anal surgical stapling device within a transanal inserter device, said transanal inserter device including a tubular member defining an open distal end portion and an open proximal end portion for slidably accommodating an intra-anal surgical stapling device therethrough, said distal end portion having a prolate distal end formed of a plurality of petal-shaped segments, said proximal end portion having a flange extending outward from said proximal end portion;
   b. inserting the inserter device and the intra-anal surgical stapling device into the anus until the flange of the inserter device rests against the perineal tissue surrounding the anus arresting further insertion of the inserter device into the anus; and
   c. urging the distal end portion of the intra-anal surgical stapling device against the segments while the inserter device is maintained in its arrested position causing said segments to move outward thereby permitting said intra-anal device to extend therethrough.

2. A method for inserting the distal end portion of an intra-anal surgical stapling device through an anus comprising the steps of:
   a. inserting a transanal inserter device through an anus, said transanal inserter device including a tubular member defining an open distal end portion and an open proximal end portion for slidably accommodating an intra-anal surgical stapling device therethrough, said distal end portion having a prolate distal end formed of a plurality of petal-shaped segments, said proximal end portion having a flange extending outward from said proximal end;
   b. arresting insertion of the transanal inserter device into the anus when the flange of the inserter device rests against the perineal tissue surrounding the anus;
   c. positioning an intra-anal surgical stapling device at the open proximal end portion of the transanal inserter device;
   d. sliding the intra-anal surgical stapling device through the transanal inserter device until the intra-anal surgical stapling device contacts the segments thereof; and
   e. urging the distal end portion of the intra-anal surgical stapling device against the segments while the inserter device is maintained in its arrested position causing the segments to move outward thereby permitting the intra-anal device to extend therethrough.

* * * * *